(12) United States Patent
Chaput et al.

(10) Patent No.: US 9,234,197 B2
(45) Date of Patent: Jan. 12, 2016

(54) GENETIC ELEMENT THAT ENHANCES PROTEIN TRANSLATION

(71) Applicant: ARIZONA BOARD OF REGENTS, a body corporate of the State of Arizona, acting for and on behalf of Ariz, Scottsdale, AZ (US)

(72) Inventors: John Chaput, Phoenix, AZ (US); Bertram Jacobs, Tempe, AZ (US); Brian Wellensiek, Glendale, AZ (US); Julia Flores, Mesa, AZ (US)

(73) Assignee: Arizona Board of Regents, A Body Corporate of the State of Arizona for and on Behalf of Arizona State University, Scottsdale, AZ (US)

( * ) Notice: Subject to any disclaimer, the term of this patent is extended or adjusted under 35 U.S.C. 154(b) by 23 days.

(21) Appl. No.: 14/349,835

(22) PCT Filed: Oct. 26, 2012

(86) PCT No.: PCT/US2012/062045
§ 371 (c)(1),
(2) Date: Apr. 4, 2014

(87) PCT Pub. No.: WO2013/063348
PCT Pub. Date: May 2, 2013

(65) Prior Publication Data
US 2014/0255990 A1    Sep. 11, 2014

Related U.S. Application Data

(60) Provisional application No. 61/552,564, filed on Oct. 28, 2011.

(51) Int. Cl.
| | | |
|---|---|---|
| *C12N 15/85* | (2006.01) | |
| *C12N 15/113* | (2010.01) | |
| *C12N 15/67* | (2006.01) | |
| C07H 21/04 | (2006.01) | |
| C12N 15/00 | (2006.01) | |
| C12N 15/86 | (2006.01) | |
| C12N 5/02 | (2006.01) | |
| C12P 21/06 | (2006.01) | |

(52) U.S. Cl.
CPC .............. *C12N 15/113* (2013.01); *C12N 15/67* (2013.01); *C12N 15/85* (2013.01); *C12N 2830/30* (2013.01); *C12N 2830/85* (2013.01); *C12N 2840/105* (2013.01); *C12N 2840/85* (2013.01)

(58) Field of Classification Search
None
See application file for complete search history.

(56) References Cited

U.S. PATENT DOCUMENTS

2003/0232442 A1    12/2003    Dobie
2013/0230884 A1*    9/2013    Chaput et al. ................ 435/69.1

FOREIGN PATENT DOCUMENTS

| WO | 2012009644 A3 | | 1/2012 | | |
| WO | WO 2012/009644 | * | 1/2012 | ............. | C12N 15/10 |

OTHER PUBLICATIONS

Hofmann et al., "Efficient gene transfer into human hepatocytes by baculovirus vectors" 92 Proceedings of the National Academy of Sciences USA 10099-10103 (1995).*
Deng et al. (1991). "High-Efficiency Protein Synthesis From T7 RNA Polymerase Transcripts in 3T3 Fibroblasts." Gene 109(2): 193-201.
Fuerst et al. (1986). "Eukaryotic Transient—Expression System Based on Recombinant Vaccinia Virus that Synthesizes Bacteriophage T7 RNA Polymerase." Proc. Natl. Acad. Sci. 83: 8122-8126.
Graham et al. (1991). "Manipulation of Adenovirus Vectors." Methods in Molecular Biology 7: 109-128.
International Search Report for PCT/US2012/062045, mailed Jan. 28, 2013.

* cited by examiner

*Primary Examiner* — Nancy J Leith
(74) *Attorney, Agent, or Firm* — McDonnell Boehnen Hulbert & Berghoff LLP

(57) ABSTRACT

The present invention provides isolated polynucleotides that can serve as translation enhancing elements and their use in protein expression reagents and methods.

13 Claims, 6 Drawing Sheets

US 9,234,197 B2

GENETIC ELEMENT THAT ENHANCES PROTEIN TRANSLATION

RELATED APPLICATIONS

This application claims priority to U.S. Provisional Patent Application 61/552,564 filed Oct. 28, 2011, incorporated by reference herein in its entirety.

STATEMENT OF U.S. GOVERNMENT INTEREST

This work was made with government support under grant number GM085530 awarded by the National Institute of Health. The U.S. government has certain rights in the invention.

SUMMARY OF THE INVENTION

In a first aspect, the present invention provides isolated polynucleotides, comprising a nucleic acid sequence according to 5'-CATATTGAAGAGACAGAGT-GATATATAAAACTGCTAA-3' (SEQ ID NO:1). In one embodiment, the nucleic acid sequence comprises 5'-AGAACCATATTGAAGAGACAGAGT-GATATATAAAACTGCTAA-3' (SEQ ID NO:2). In another embodiment, the nucleic acid sequence comprises 5'-AGAACCATATTGAAGAGACAGAGT-GATATATAAAACTGCTAACTCAA GCAGCACAA-GAATTAAATGAATACCAAGAAAATACTTGGCCAG-3' (SEQ ID NO:3). In a further embodiment, the polynucleotide is 200 nucleotides or less in length.

In a second aspect, the present invention provides expression vectors, comprising the isolated polynucleotide of any embodiment of the first aspect of the invention, operatively linked to a protein coding region.

In a third aspect, the present invention provides expression vectors comprising
 (a) the isolated polynucleotide of any embodiment of the first aspect of the invention; and
 (b) a cloning site suitable for cloning of a protein-encoding nucleic acid of interest located downstream of the isolated polynucleotide.

In one embodiment, the expression vector further comprises a promoter located upstream of the isolated polynucleotide. In another embodiment, the expression vector further comprises a protein-encoding nucleic acid cloned into the cloning site.

In a fourth aspect, the invention provides recombinant host cells comprising the expression vector of embodiment of the third aspect of the invention. In a further embodiment, the invention provides recombinant viruses, including but not limited to recombinant infectious vaccinia virus, comprising an expression vector of the invention.

In a fifth aspect, the present invention provides methods for protein expression, comprising contacting the expression vector of any embodiment of the fourth aspect of the invention or the recombinant host cells of any embodiment of the fourth aspect of the invention, with reagents and under conditions suitable for promoting expression of the polypeptide encoded by the protein-encoding nucleic acid. In one embodiment, the protein expression is carried out in a cell-free translation system. In another embodiment, the expression vector comprises a recombinant vaccinia virus. In a further embodiment, the method comprises non-viral-mediated translation in the recombinant host cell.

DETAILED DESCRIPTION OF THE INVENTION

Figure 1:
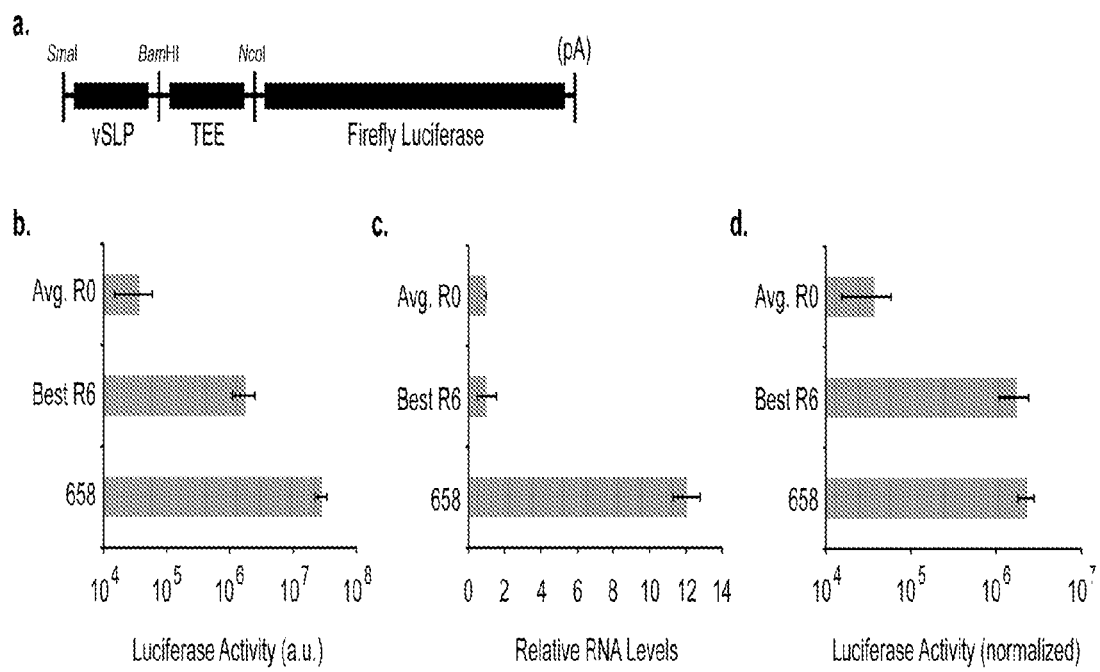
FIG. 1. Functional analysis of hTEE-658. (a) Schematic view of the firefly luciferase reporter used to evaluate human in vitro selected translation enhancing elements in a cytoplasmic expression system. vSLP refers to vaccinia synthetic late promoter and TEE refers to translation enhancing element. (b) Luciferase expression levels obtained using vectors that contain either four randomly chosen sequences from the naïve pool (Avg. R0), nine high activity sequences discovered by in vitro selection (Best R6), or hTEE-658 in the 5'UTR of the primary transcript. (c) Real-time quantitative PCR analysis of reverse-transcribed luciferase mRNA normalized to reverse-transcribed GAPDH. (d) Luciferase values normalized to cellular RNA levels.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

All embodiments disclosed herein can be combined with other embodiments unless the context clearly dictates otherwise.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Additionally, the words "herein," "above," and "below" and words of similar import, when used in this application, shall refer to this application as a whole and not to any particular portions of this application. As used herein, the singular forms "a", "an" and "the" include plural referents unless the context clearly dictates otherwise. "And" as used herein is interchangeably used with "or" unless expressly stated otherwise.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments.

In a first aspect, the present invention provides isolated polynucleotides, comprising or consisting of a nucleic acid sequence according to 5'-CATATTGAAGAGACAGAGT-GATATATAAAACTGCTAA-3' (SEQ ID NO:1), complements thereof, or RNA expression products thereof.

As disclosed in the examples that follow, the polynucleotides according to this aspect of the invention form a core polynucleotide that can be used to dramatically enhance transgene expression in recombinant cells, such as mammalian cells. In one embodiment, the isolated polynucleotide comprises or consists of

5'-AGAACCATATTGAAGAGACAGAGT-GATATATAAAACTGCTAA-3' (SEQ ID NO:2).

In another embodiment, the isolated polynucleotide comprises or consists of 5'-AGAACCATATTGAAGAGACA-GAGTGATATATAAAACTGCTAACTCAA GCAGCA-CAAGAATTAAATGAATACCAAGAAAATACTTG GCCAG-3' (SEQ ID NO:3).

The polynucleotide may be of any suitable length. In one embodiment, the polynucleotide is 200 nucleotides or less in length. In various embodiments, the isolated polynucleotides are less than 190, 180, 170, 160, 150, 140, 130, 120, 110, 100, 90, 80, 70, 60, 50, or 40 nucleotides in length. In another embodiment, the isolated polynucleotides consist of the recited sequence.

The polynucleotides may be single or double stranded, and may be DNA, or RNA. The polynucleotides may comprise additional sequences useful for promoting expression and/or purification of the encoded protein, including but not limited to polyA sequences, modified Kozak sequences, detectable labels, and sequences encoding epitope tags, export signals, and secretory signals, nuclear localization signals, and plasma membrane localization signals.

In a second aspect, the present invention provides expression vectors, comprising the isolated polynucleotide of any embodiment or combination of embodiments of the first aspect of the invention, operatively linked to a protein coding region or to a cloning site suitable for cloning of a protein coding region. As demonstrated in the examples that follow, the polynucleotides of the invention can be used to dramatically enhance expression of a transgene to which it is operatively linked. For example, when used in combination with vaccinia virus expression systems, no separate promoter sequence is required, as the polynucleotides of the invention appear to function as promoters for the vaccinia virus RNA polymerase, in addition to providing significant translational enhancement.

The construction of expression vectors for use in transfecting prokaryotic and eukaryotic cells is well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In one embodiment, the expression vector comprises a plasmid; in another embodiment, the expression vectors are viral vectors, such as recombinant vaccinia vectors with the polynucleotide inserted into the viral genome at an appropriate location to drive expression of a recombinant protein of interest.

In one embodiment, the expression vector is a vaccinia virus expression vector. Vaccinia virus (VACV or VV) is a large, complex, enveloped virus belonging to the poxvirus family. It has a linear, double-stranded DNA genome of approximately 190 kb in length, which encodes for around 250 genes. The genome is surrounded by a lipoprotein core membrane. The poxviruses are the largest known DNA viruses and are distinguished from other viruses by their ability to replicate entirely in the cytoplasm of the host cell, outside of the nucleus. VV can accept as much as 25 kb of foreign DNA, making it useful for expressing large genes. Foreign genes are integrated stably into the viral genome, resulting in efficient gene expression. Other viral expression vectors for use in the present invention include, but are not limited to, certain highly attenuated, host-restricted, non- or poorly replicating poxvirus strains have been developed for use as substrates in recombinant vaccine development. These strains include the Orthopoxviruses, Modified Vaccinia Ankara (MVA) and NYVAC (derived from the Copenhagen vaccinia strain), and the Avipoxviruses, ALVAC and TRO-VAC (derived from canarypox and fowlpox viruses, respectively).

As used herein, a "protein coding region" is any nucleic acid sequence, such as a DNA sequence, encoding a polypeptide product. As will be understood by those of skill in the art, the vectors of the invention can be used to drive expression of any polypeptide product of interest.

As used herein, "operatively linked" means the association of two or more nucleic acid fragments on a single polynucleotide so that the function of one is affected by the other. For example, the polynucleotide is operatively linked with a coding sequence (or cloning site into which a coding region may be cloned) when it is capable of affecting the expression of that coding sequence (transcription and/or translation). Coding sequences can be operatively linked to regulatory sequences in sense or antisense orientation. The polynucleotide is preferably located 5' to the protein coding region for operative linking to the protein coding region (or cloning site)

In one embodiment, the expression vector does not include an additional promoter sequence operatively linked to the protein coding region (or cloning site); this is particularly preferred for use with a vaccinia virus expression system, such as is known in the art. See, for example, Fuerst et al., PNAS 83:8122-8126 (1986). In one embodiment, the vaccinia virus expression system comprises a recombinant vaccinia virus that has been engineered to express the gene of interest when used to infect cells. In this embodiment, the expression vector of the invention comprises a recombinant vaccinia virus in which the isolated polynucleotide of any embodiment or combination of embodiments of the first aspect of the invention is operatively linked to a protein coding region or to a cloning site suitable for cloning of a protein coding region. In another embodiment, the expression vector is a plasmid in which the isolated polynucleotide of any embodiment or combination of embodiments of the first aspect of the invention is operatively linked to a protein coding region or to a cloning site suitable for cloning of a protein coding region; in this embodiment, the plasmid is transfected into a vaccinia virus infected cell.

In another embodiment, the expression vector further comprises a promoter sequence located 5' to the polynucleotide in the expression vector. This embodiment can be used in combination with any other embodiment herein, including but not limited to in systems where the polynucleotide acts as a promoter. As used herein, a "promoter" is any DNA sequence that can be used to help drive RNA expression of a DNA sequence downstream of the promoter. Suitable promoters include, but are not limited to, the T7 promoter, SP6 promoter, CMV promoter, and vaccinia virus synthetic-late promoter. As will be understood by those of skill in the art, a given double stranded DNA construct may contain more than one promoter, as appropriate for a given proposed use. In one embodiment, an inducible promoter is used; this embodiment can be used in combination with any other embodiment herein, including but not limited to when the expression vector is not used in combination with the vaccinia virus system or other expression system where the polynucleotide itself acts as a promoter. Given the significant enhancement in protein translation that the polynucleotides of the invention provide, the use of an inducible promoter can be beneficial to, for example, control expression of proteins that might otherwise be toxic to the host cells.

It will be understood by those of skill in the art that the constructs of the invention may comprise further nucleotide elements as appropriate for a given intended use, including but not limited to primer binding sites, restriction enzyme recognition sites, etc.

In a third aspect, the present invention provides recombinant host cells comprising an expression vector of any embodiment or combination of embodiments of the invention. Such host cells can be used, for example, to prepare large amounts of the expression vector and to provide for expression of the encoded proteins in the host cells. Any suitable host cell may be used, including but not limited to bacterial host cells (particularly preferred for large scale production of the expression vectors) and eukaryotic host cells, including but not limited to mammalian and human cells, which are particularly preferred for use in methods for producing a protein of interest using the expression vectors of the invention. Exemplary mammalian host cells for use include, but are not limited to, Chinese hamster ovary (CHO) cells, Baby hamster kidney (BHK) cells, myeloma cells, HEK-293 cells, HeLa cells, mouse cells, Vero cells, and PER.C6 cells. The host cells may further comprise any other components that would be of value for a particular use. In one embodiment, mammalian (preferably human) host cells comprise a non-vaccinia expression vector of the invention, and are infected with vaccinia virus prior to protein production. In another embodiment, mammalian (preferably human) host cells are infected with the recombinant vaccinia expression vector of the invention prior to protein production.

In a further embodiment, the invention provides recombinant viruses, including but not limited to recombinant infectious vaccinia virus, comprising the expression vector of any embodiment or combination of embodiments of the invention, where the expression vector comprises a viral expression vector, such as a vaccinia virus expression vector. Methods for selecting the recombinant viruses of the invention are well within the level of skill in the art based on the teachings herein in light of the general knowledge in the art.

In a fourth aspect, the present invention provides methods for protein expression, comprising contacting an expression vector comprising a protein coding region according to any embodiment or combination of embodiments of the invention, with reagents and under conditions suitable for promoting expression of the polypeptide encoded by the protein coding region. It is within the level of skill in the art to choose appropriate reagents and conditions for RNA expression from the expression construct, followed by translation of the encoded polypeptide. Exemplary reagents and conditions are described in the examples that follow. The methods of this aspect of the invention may be carried out in a cell free translation system or in vivo. In a preferred embodiment, the protein expression is carried out in a recombinant host cell of the invention. In one embodiment, mammalian (preferably human) host cells comprise a non-vaccinia expression vector of the invention, and are infected with vaccinia virus prior to protein production; see, for example, Fuerst et al., PNAS 83:8122-8126 (1986). In another embodiment, mammalian (preferably human) host cells are infected with the recombinant vaccinia expression vector of the invention prior to protein production. In another embodiment, the recombinant host cells comprise a non-vaccinia expression vector of the invention, and the method comprises non-viral mediated translation in the recombinant host cell (ie: no infection with vaccinia virus prior to protein production).

As described in the examples that follow, the polynucleotides of the invention can function as vaccinia virus promoters, as well as translational enhancers, thus simplifying the expression system required for large scale protein expression in mammalian cells.

EXAMPLE 1

Materials and Methods

Luciferase Reporter Assay
HeLa, BHK, or HEK-293 cells were seeded at a density of 15,000 cells per well in white 96-well plates 18 hours prior to transfection. Cells were transfected with a complex of the luciferase reporter plasmid (200 ng) and LIPOFECTAMINE® 2000 (0.5 µl) in OPTI-MEM® (Invitrogen), and immediately infected with the VC2, MVA, or vTF7-3 strains of vaccinia virus at a multiplicity of infection (m.o.i) of 5 PFU/cell for all six hour assays and 30 PFU/cell for 24 hour time course assays. Cells were lysed at 6 hours post-infection (unless otherwise indicated) in the 96-well plates and luciferase activity was measured using the Promega Luciferase Assay System with a GLOMAX® microplate luminometer (Promega).

Western Blot

For protein isolation, HeLa cells were plated at a density of 200,000 cells per well in a 24 well plate 18 hours prior to transfection. Cells were transfected with a complex of 800 ng of plasmid and 2 µl of LIPOFECTAMINE® 2000 in OPTI-MEM®. Transfected cells were immediately infected with the Copenhagen strain (VC-2) of WT vaccinia virus at a multiplicity of infection (m.o.i) of 5 PFU/cell. Cells were lysed 6 hours post-infection with Passive Lysis Buffer (Promega). Cellular debris was removed by centrifugation for 10 min at 10,000 rcf and the supernatant containing the protein of interest was removed and stored at −80° C. For protein analysis, the supernatant was diluted with NUPAGE 4×LDS sample buffer (Invitrogen) and proteins were denatured by heating for 10 rain at 95° C. before being run on a NUPAGE® 4-12% Bis-Tris gel (Invitrogen). Proteins were transferred to a nitrocellulose membrane using the IBLOT Gel Transfer system (Invitrogen), and the membrane was blocked for 1 hour at 24° C. in TBS-TWEEN® (20 mM Tris, 125 mM NaCl, pH 7.5, and 0.05% TWEEN®) supplemented with 3% milk. The appropriate primary antibodies were incubated with the membrane in TBS-TWEEN® with 3% milk overnight at 4° C. Anti-luciferase, anti-GAPDH and anti-myc antibodies were obtained commercially (Abcam and Millipore), while the HIV-1 Gag antibody was obtained from Professor Dr. Hohne at the Charite Institute for Biochemie in Berlin, Germany. Goat-anti-mouse or goat-anti-rabbit HRP conjugated secondary antibodies (Bethyl Laboratories) were then incubated with the membranes for one hour at room temperature. Membranes were visualized with SUPERSIGNAL® West Pico or Dura Chemiluminescent Substrate (Pierce Biotechnology).

Vaccinia Virus Strains

The vaccinia virus Copenhagen (VC2) and vTF7-3 viral strains were obtained from ATCC. The modified vaccinia virus Ankara (MVA) was obtained from Sanofi Pasteur. VC2 is considered a wild type vaccinia virus, MVA is an attenuated vaccinia virus strain that is non-pathogenic in humans, and vTF7-3 is a recombinant vaccinia virus strain that has been engineered to express T7 RNA polymerase.

Recombinant protein expression is essential to biotechnology and molecular medicine, but methods to obtain significant quantities of folded and functional protein in mammalian cell culture have been lacking. Here we describe a novel 37-nucleotide sequence that promotes unusually high levels of transgene expression in a vaccinia virus cytoplasmic expression system. This sequence was discovered by screening hundreds of in vitro selected sequences in a vaccinia-driven transfect-infect assay. Vectors carrying the motif in the 5' untranslated region produce >1,000-fold more protein than equivalent vectors containing conventional vaccinia promoters. Initial mechanistic studies indicate that high protein expression results from dual activity that impacts both transcription and translation. We suggest that this motif represents a powerful new tool in vaccinia-based protein expression and vaccine development technology.

Vaccinia virus (VACV), a member of the poxvirus family, received worldwide attention when it was used in the 1970's to eradicate viriola virus, the causative agent of smallpox. Since then, VACV has been used for biotechnology purposes that include mammalian protein expression and the design of therapeutic vaccines directed against infectious agents and cancer. VACV has a number of unique properties that make it attractive for these types of applications. First, unlike most DNA viruses, the VACV genome is not recognized by cellular enzymes and therefore cannot infect the host cell. Second, transgene expression occurs exclusively in the cytoplasm of infected cells using its own enzymes for DNA replication and RNA transcription. The ability to circumvent nuclear expression and processing allows VACV to infect a wide range of cell types and significantly reduces the period of time required to obtain recombinant protein in mammalian cell culture. Third, proteins expressed in VACV systems have correct patterns of post-translational modifications because foreign genes are expressed in cells from their species of origin or relevant host system. This attribute is important as expression systems, like baculovirus can produce modifications at alternative sites, which can obfuscate protein function and immunogenicity.

Previously we have used mRNA display to interrogate the entire human genome for RNA motifs that function with cap-independent translation initiation activity. From an enriched pool of ~1000 human sequences, motifs with perfect identity to the human reference genome (~250 sequences) were assayed for luciferase activity in HeLa cells. We found that the most active sequences could enhance translation by up to 100-fold after RNA normalization. These results are summarized in FIG. 1.

Motivated by the potential to enhance protein expression levels, we screened hundred of additional sequences for translation enhancing activity vaccinia-based cytoplasmic expression system. This screen led to the identification of a sequence (hTEE-658), which when placed in the 5'UTR yields >1,000-fold more protein than similar vectors carrying an unselected sequence of similar length and ~20-50-fold more protein than our best translation enhancing element discovered to date. The increased protein levels in the hTEE-658 vector is due to increases of both RNA transcription and protein translation.

Figure 2:
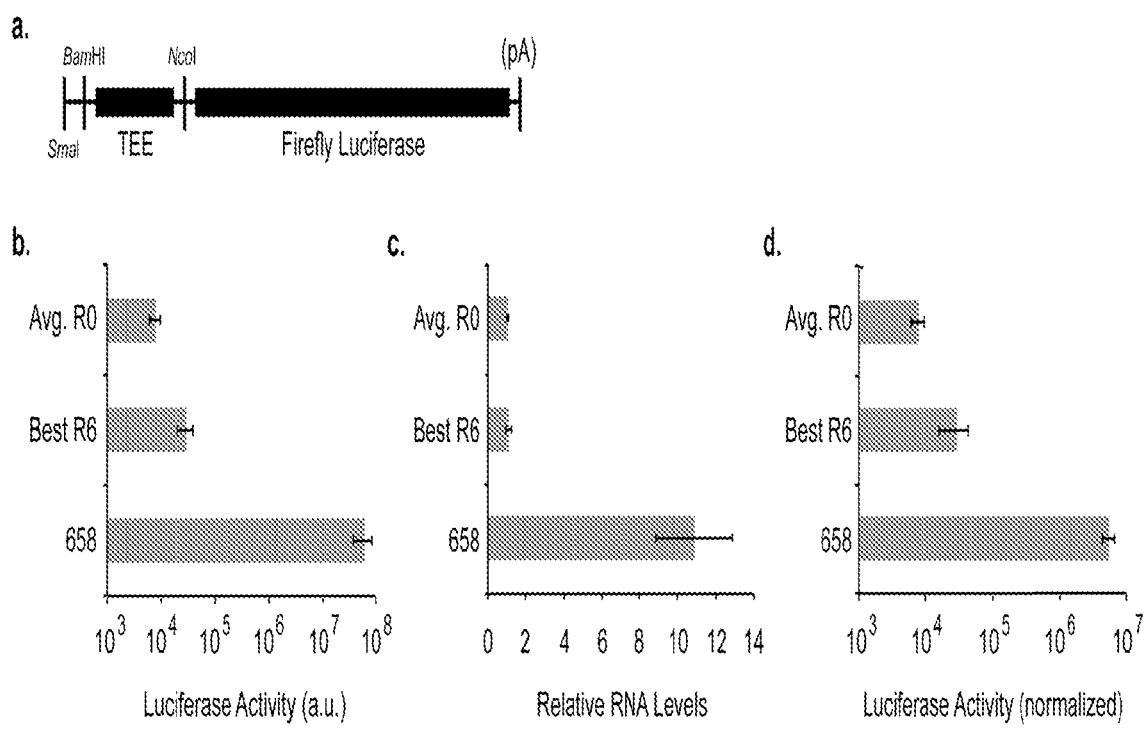
FIG. 2. Functional analysis of the hTEE-658 vector missing viral promoter. (a) Schematic view of a firefly luciferase reporter missing the vaccinia virus synthetic late promoter. (b) Luciferase expression levels obtained using vectors that contain either four randomly chosen sequences from the naïve pool (Avg. R0), nine high activity sequences discovered by in vitro selection (Best R6), or hTEE-658 in the 5'UTR of the primary transcript. (c) Realtime quantitative PCR analysis of reverse-transcribed luciferase mRNA normalized to reverse-transcribed GAPDH. (d) Luciferase values normalized to cellular RNA levels.

We confirmed the ability of hTEE-658 to function as a vaccinia virus promoter by measuring protein translation levels using a knockout plasmid missing the viral promoter. A diagram of the promoter-less plasmid is seen in FIG. 2a, it only contains hTEE-658 and Luciferase; there are no other known promoters present in the plasmid. Our standard luciferase reporter assay was used to determine activity. As expected, the vector carrying hTEE-658 yielded ultrahigh levels of protein, while the control vectors remained low. (FIG. 2)

Figure 3:
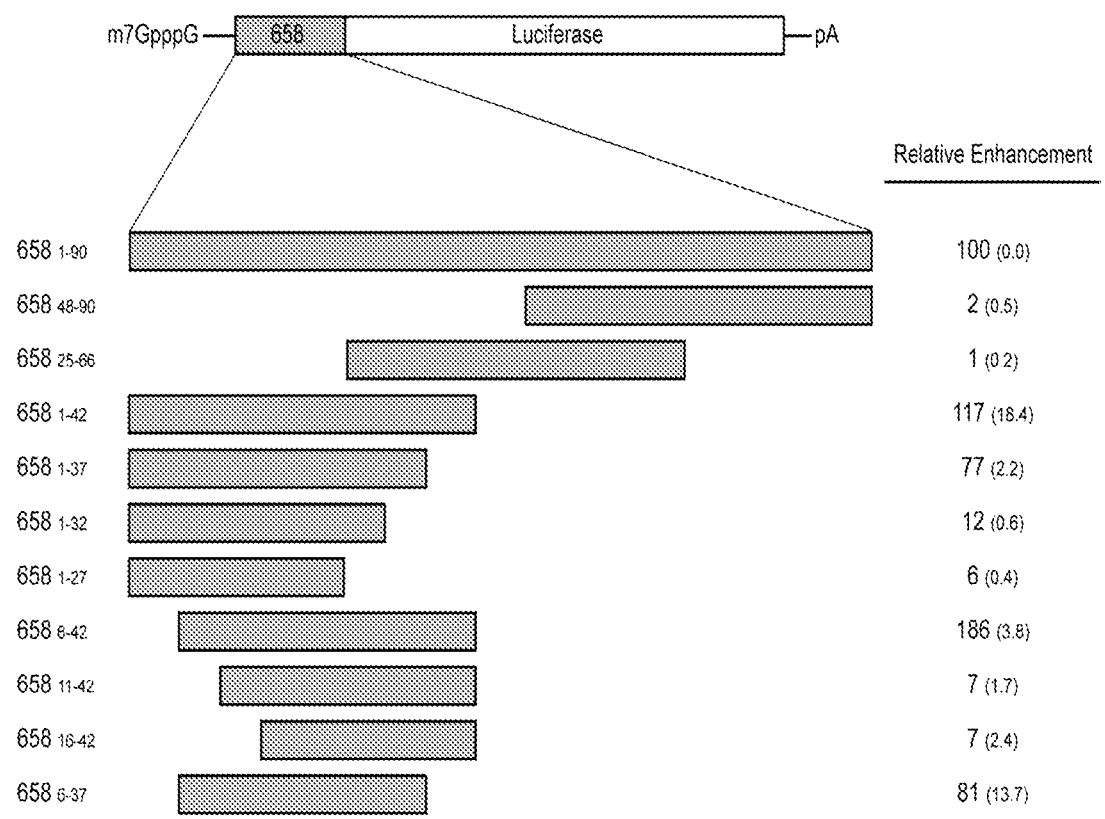
FIG. 3. End-mapping deletion analysis of hTEE-658. Monocistronic constructs containing deletions of the 5' and 3' ends were analyzed to identify the core functional domain of hTEE-658. Subscript labels indicate the precise nucleotide fragment analyzed for activity. Translation activity is represented as a percentage relative to the full length TEE-658 sequence. The normalized percent error is shown in parenthesis.

We next determined the minimal nucleotide sequence responsible for hTEE-658 activity by sequentially removing small nucleotide segments from the 5' and 3' ends (FIG. 3). The core functional domain consists of 37 nucleotides located between positions 6 and 42 of the full length sequence.

Full length 658:

(SEQ ID NO: 3)
5'-AGAACCATATTGAAGAGACAGAGTGATATATAAAACTGCTAACTC

AAGCAGCACAAGAATTAAATGAATACCAAGAAAATACTTGGCCAG-3'

658 core region:

(SEQ ID NO: 1)
5'-CATATTGAAGAGACAGAGTGATATATAAAACTGCTAA-3'

Figure 4:
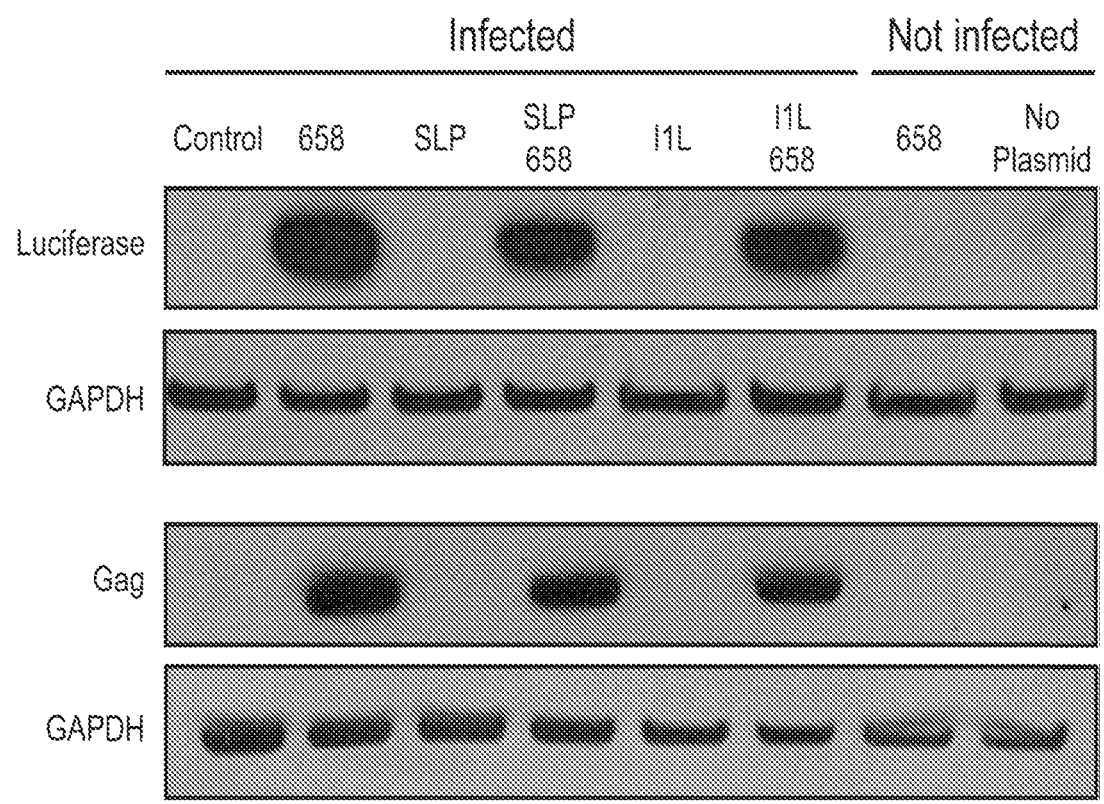
FIG. 4. Expression of luciferase and HIV Gag proteins. Relative luciferase and HIV Gag protein levels produced by expression vectors carrying hTEE-658 core, SLP, I1L, or a combination of hTEE-658 with either SLP or I1L in the 5'UTR of the primary transcript. HeLa cells were transfected with each vector and immediately infected with vaccinia virus. Protein levels were determined after 6 hours by western blot analysis using antibodies directed against luciferase and HIV Gag. A third antibody directed against glyceraldehyde-3-phosphate dehydrogenase was used as a control for sample loading. Additional controls include uninfected samples that were either transfected with the hTEE-658 vector or left untreated.

We next measured the amount of recombinant protein produced by hTEE-658 relative to conventional vaccinia promoters SLP and I1L. Relative luciferase and HIV Gag protein levels produced by expression vectors carrying hTEE-658 core, SLP, I1L, or a combination of hTEE-658 with either SLP or I1L in the 5'UTR of the primary transcript. HeLa cells were transfected with each vector and immediately infected with vaccinia virus. Protein levels were determined after 6 hours by western blot analysis using antibodies directed against luciferase and HIV Gag. A third antibody directed against glyceraldehyde-3-phosphate dehydrogenase was used as a control for sample loading. Ultrahigh protein is obtained only when the core sequence is present either alone or in combination with known vaccinia promoters (FIG. 4). Overexposed gels reveal trace amounts of protein for the SLP and I1L promoters, consistent with translation values observed in FIGS. 1 and 2 (data not shown).

We then compared luciferase expression driven by hTEE-658 compared to the EMCV IRES (Internal Ribosomal Entry Site (IRES) from the Encephalomyocarditis virus (EMCV)) over the course of 24 hours. The EMCV IRES is regarded as the best translation enhancing sequence known to-date, which is why we chose it for comparison.

Figure 5:
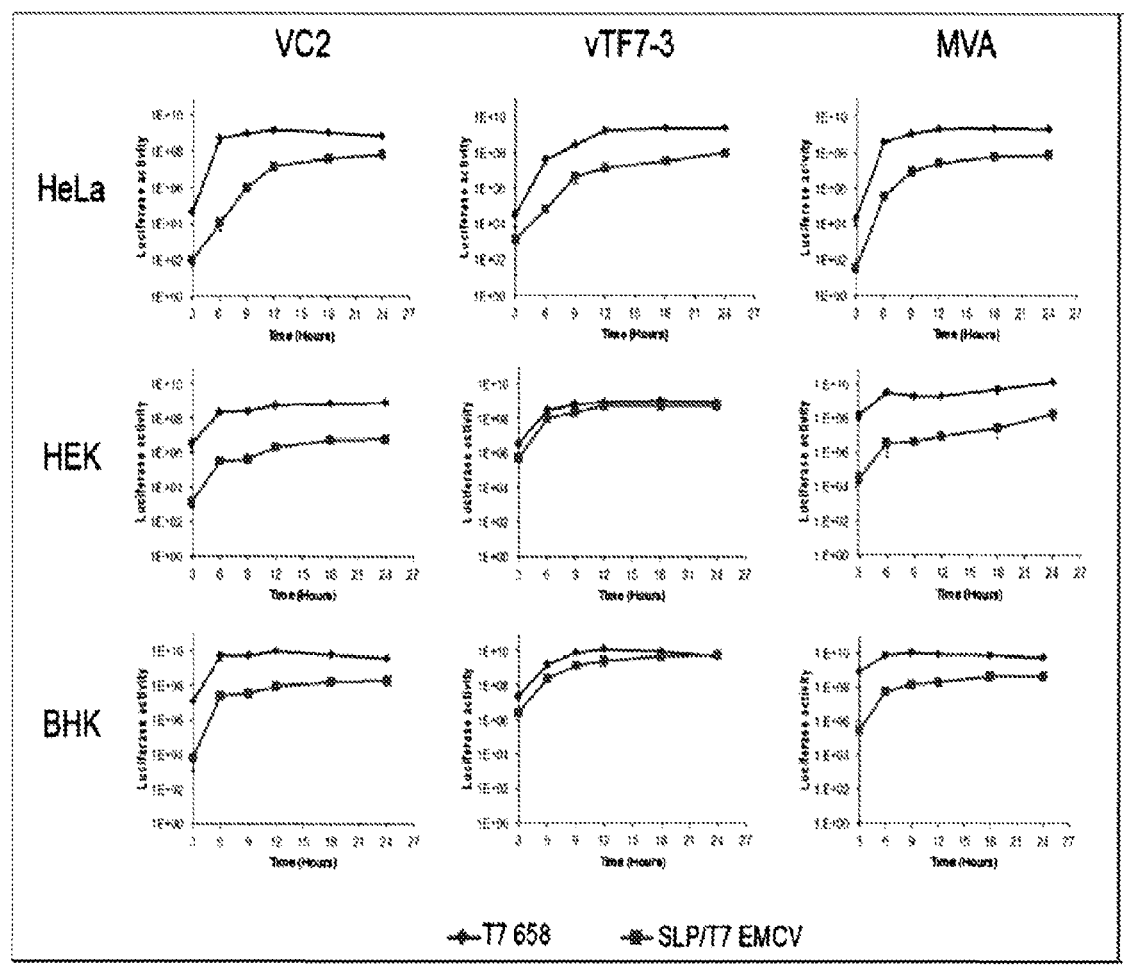
FIG. 5. hTEE-658 driven protein expression profile. Luciferase expression driven by hTEE-658 compared to the EMCV IRES over the course of 24 hours. Transfect/infect assays were conducted in three different cell lines (HeLa, HEK 293T, and BHK) with three different vaccinia virus strains (VC2, vTF7.3, and MVA). Depending upon the virus used, the promoter for the EMCV construct was either the vaccinia synthetic late promoter (SLP, used with VC2 and MVA) or T7 (used with vTF7-3).

Transfect/infect assays were conducted in three different cell lines (HeLa, HEK 293T, and BHK) with three different vaccinia virus strains (VC2, vTF7.3, and MVA). Depending upon the virus used, the promoter for the EMCV construct was either the vaccinia synthetic late promoter (SLP, used with VC2 and MVA) or T7 (used with vTF7-3). Our results (FIG. 5) show that our hTEE-658 driven system can outperform the best known system available.

Figure 6:
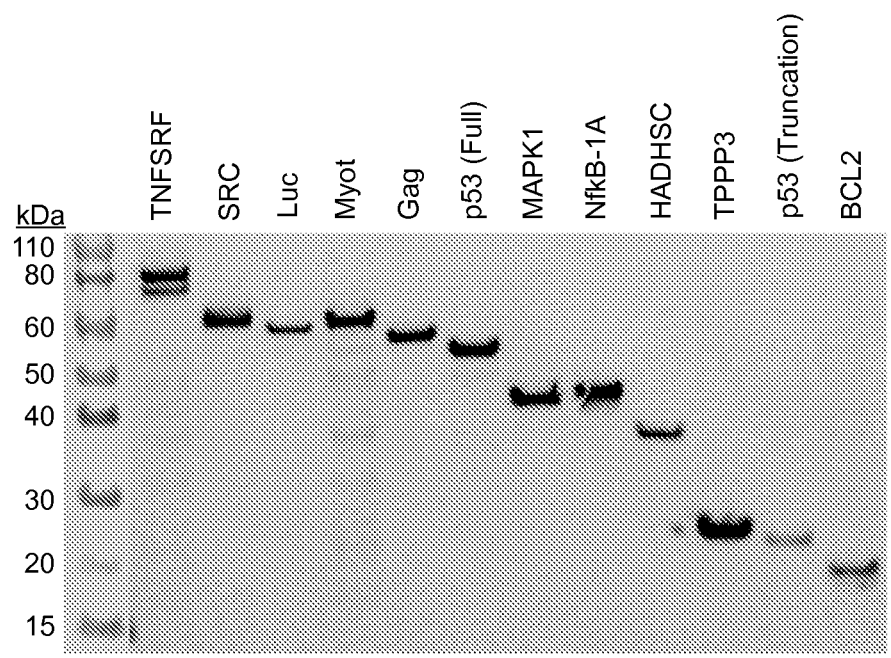
FIG. 6. hTEE-658 driven expression of different targets. Twelve different proteins were expressed in HeLa cells by transfect/infect. Each expression construct contained hTEE-658 upstream of the coding region, as well as a downstream c-myc affinity tag. Cells were lysed 6 hours post-infection and protein was detected by Western blot. Each band was consistent with the expected size of the protein of interest.

We then measured expression of twelve different proteins expressed in Hela cells by transfect/infect using the hTEE-658 system. Each band was consistent with the expected size of the protein of interest (FIG. 6).

TABLE 1

| Gene | Information |
| --- | --- |
| TNFSRF | Tumor necrosis factor receptor superfamily member 21; 1 member from a family of cell surface receptors involved in extra-cellular communication and apoptosis. |
| SRC | Proto-oncogene tyrosine-protein kinase; Non-receptor tyrosine kinase involved in growth regulation and known to be a proto-oncogene. |
| Luc | Firefly luciferase. |
| Myot | Myotilin; Structural muscle protein involved in actin bundle formation. |
| Gag | HIV-1 Gag. |
| p53 | Protein 53; Tumor suppressor gene that functions to induce growth arrest or apoptosis, involved in cell cycle regulation as a trans-activator which controls transcription of various genes. |
| MAPK1 | Mitogen-Activated Protein Kinase 1; Serine/threonine kinase which acts as an essential component of the MAP kinase signal transduction pathway. |
| NFkB-1A | Nuclear Factor kappa B; Protein involved in a multimeric complex that helps to regulate gene transcription, has been linked with inflammation and cancer. |
| HADHSC | 3-hydroxyacyl-CoA dehydrogenase; functions in the mitochondrial matrix to catalyze the oxidation of straight-chain 3-hydroxyacyl-CoAs as part of the beta-oxidation pathway. |
| TPPP3 | Tubulin Polymerization-Promoting Protein family member 3; Binds tubulin and has microtubule bundling activity. May play a role in cell proliferation and mitosis. |
| BCL2 | B-cell lymphoma 2; Anti-apoptotic protein that binds BAD and BAK proteins to form dimers in the mitochondrial membrane and prevent the release of cytochrome C and other apoptotic factors from the mitochondria. |

We claim:

1. A recombinant viral or plasmid expression vector comprising
   (a) a translation enhancement element (TEE) of between 37 and 42 nucleotides in length, comprising the nucleic acid sequence of 5'-CATATTGAAGAGACAGAGTGATATATAAAACTGCTAA-3' (SEQ ID NO: 1); and
   (b) a cloning site located downstream of the TEE.

2. The expression vector of claim 1, further comprising a promoter located upstream of the TEE.

3. The expression vector of claim 1, further comprising a protein encoding nucleic acid cloned into the cloning site.

4. An isolated recombinant host cell comprising the expression vector of claim 1.

5. A method for protein expression, comprising contacting the expression vector of claim 3 with reagents and under conditions for promoting expression of the protein encoded by the protein-encoding nucleic acid, and expressing the protein.

6. The method of claim 5, wherein the protein is expressed in a cell-free translation system.

7. The method of claim 5, wherein the protein is expressed by a recombinant host cell.

8. The method of claim 5, wherein the expression vector is a recombinant vaccinia virus.

9. The method of claim 7, wherein the recombinant host cell expresses the protein using non-viral-mediated translation.

10. An isolated recombinant virus, comprising the expression vector of claim 1, wherein the expression vector is comprises a viral expression vector.

11. The recombinant virus of claim 10, wherein the recombinant virus is a vaccinia virus, and the viral expression vector is a vaccinia virus expression vector.

12. The expression vector of claim 1, wherein the TEE consists of 5'-CATATTGAAGAGACAGAGTGATATATAAAACTGCTAA-3' (SEQ ID NO: 1).

13. The expression vector of claim 1, wherein the TEE consists of 5'-AGAACCATATTGAAGAGACAGAGTGATATATAAAACTGCTAA-3' (SEQ ID NO:2).

* * * * *

SEQUENCE LISTING

```
<160> NUMBER OF SEQ ID NOS: 3

<210> SEQ ID NO 1
<211> LENGTH: 37
<212> TYPE: DNA
<213> ORGANISM: Artificial Sequence
<220> FEATURE:
<223> OTHER INFORMATION: Synthetic

<400> SEQUENCE: 1
catattgaag agacagagtg atatataaaa ctgctaa                                37

<210> SEQ ID NO 2
<211> LENGTH: 42
<212> TYPE: DNA
<213> ORGANISM: Artificial Sequence
<220> FEATURE:
<223> OTHER INFORMATION: Synthetic

<400> SEQUENCE: 2
agaaccatat tgaagagaca gagtgatata taaaactgct aa                          42

<210> SEQ ID NO 3
<211> LENGTH: 90
<212> TYPE: DNA
<213> ORGANISM: Artificial Sequence
<220> FEATURE:
<223> OTHER INFORMATION: Synthetic
```

```
<400> SEQUENCE: 3
agaaccatat tgaagagaca gagtgatata taaaactgct aactcaagca gcacaagaat       60
taaatgaata ccaagaaaat acttggccag                                       90
```